United States Patent [19]

Landgraf et al.

[11] Patent Number: 4,462,803
[45] Date of Patent: Jul. 31, 1984

[54] DEVICE FOR CLEANING TEETH

[75] Inventors: Hermann Landgraf, Heppenheim; Josef Hain, Laudenbach, both of Fed. Rep. of Germany

[73] Assignee: Siemens Aktiengesellschaft, Berlin & Munich, Fed. Rep. of Germany

[21] Appl. No.: 408,124

[22] Filed: Aug. 13, 1982

[30] Foreign Application Priority Data

Aug. 14, 1981 [DE] Fed. Rep. of Germany ....... 3132291

[51] Int. Cl.$^3$ .............................................. A61C 3/02
[52] U.S. Cl. ...................................... 433/88; 433/125; 51/439
[58] Field of Search ............ 433/80, 82, 88, 125, 433/216; 51/317, 439

[56] References Cited

U.S. PATENT DOCUMENTS

| 2,874,470 | 2/1959 | Richards | 433/88 X |
| 3,972,123 | 8/1976 | Black | 433/88 |
| 4,174,571 | 11/1979 | Gallant | 433/216 |

FOREIGN PATENT DOCUMENTS

| 1416921 | 10/1968 | Fed. Rep. of Germany | 433/80 |
| 2911629 | 9/1980 | Fed. Rep. of Germany | 51/439 |
| 999800 | 2/1952 | France | 51/439 |

Primary Examiner—Robert P. Swiatek
Attorney, Agent, or Firm—Hill, Van Santen, Steadman & Simpson

[57] ABSTRACT

A device for cleaning teeth by projecting water and a carrier gas containing an abrasive at the surface characterized by a nozzle having at least one water discharge aperture and a gas discharge aperture adjacent the water discharge aperture, the water discharge aperture being connected to a source of water, the gas discharge aperture being connected to a mixing chamber which in turn is connected by a channel to a source of carrier gas containing abrasive and by a separate channel to an additional source of abrasive-free gas which is directed into the mixing chamber through an acceleration jet so that the abrasive-free gas having a higher acceleration energy in comparison to the carrier gas mixes with the carrier gas to accelerate it as the abrasive-free gas passes through the mixing chamber and the discharge aperture.

7 Claims, 5 Drawing Figures

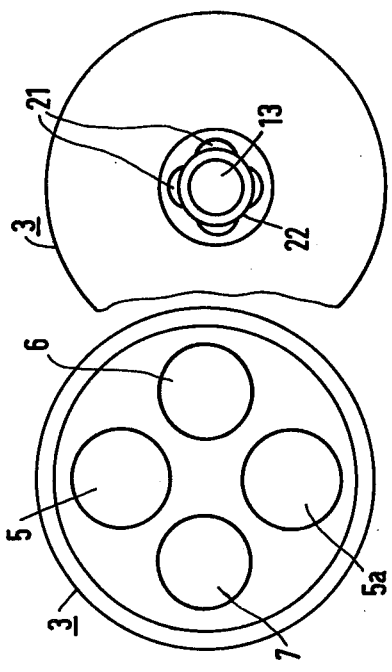
FIG 5
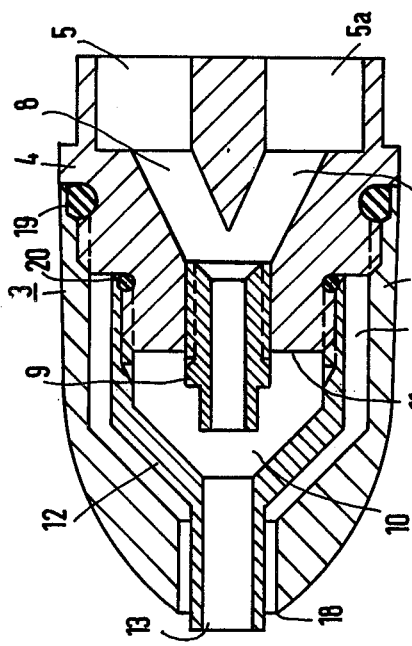
FIG 4
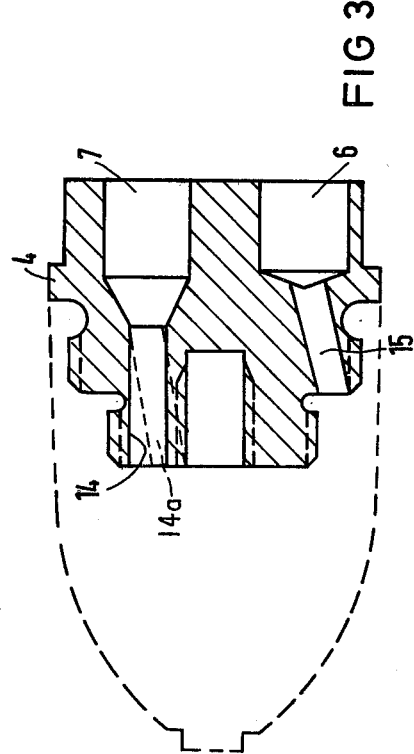
FIG 2
FIG 3

DEVICE FOR CLEANING TEETH

BACKGROUND OF THE INVENTION

The present invention is directed to a device for processing a surface of an object, such as cleaning teeth, by means of directing water and a carrier gas containing an abrasive onto the surface being processed. The device includes a nozzle having a water channel terminating in a water discharge aperture and a separate carrier gas discharge aperture which is in communication with an arrangement for conveying the carrier gas with the abrasive from a source through the nozzle.

Devices, which direct water and a carrier gas containing an abrasive, are employed among other things for the elimination of plaque or for dulling dental bridges. Various materials come into consideration as the abrasive. Water-soluble materials, for example, sodium carbonate, have proven advantageous for prophylactic tooth treatment in the patient's mouth, for example, the removal of deposits from the teeth.

In a known device, a nozzle arrangement is situated at the free end of a handle and has a channel containing a carrier gas, which contains a dry abrasive or abradant, and a second separate channel containing water. These two channels discharge from separate discharge apertures with the water discharge channel having an aperture or series of apertures that concentrically surround the discharge aperture of the carrier gas and project so as to converge onto the stream of carrier gas. An example of this type of device is disclosed in U.S. Pat. No. 4,174,571.

Practice has shown on one hand that devices of this type have a tendency either for a blockage of the channels or for an encrustation of the channels to occur at the discharge location. This is particularly true when the discharge aperture inadvertently comes into contact with the processing surface such as the tooth. As a result of such contact, a backup occurs and a mixing of the dry abrasive with the water can occur before discharge from the nozzle. Such a mixing has a consequence that if particularly given long standstill times the abrasive cakes on the walls of the channels and apertures of the nozzle.

On the other hand, it has been shown that the erosive effect or respectively the cleansing effect in the known devices is not satisfactory when based upon appropriate gas and abrasive consumption which is not too high. In order to achieve a reasonable transport of the abrasive and in order to prevent blockage of the abrasive channel, a relatively large cross-section for both the channel and discharge aperture is required. Thus, it is only possible to achieve a satisfactory abrasive effect given the known device with a relatively high gas pressure and a large amount of gas or respectively with a greatly reduced abrasive additive given in a justifiable gas consumption. However, to provide a large amount of gas will result in a bulky arrangement which will impair the viewing of the processing surface as well as making it necessary to require an increase in the extraction of gas and fluid during the treatment of the mouth of the patient.

SUMMARY OF THE INVENTION

The present invention is directed to providing an improved device for directing a stream of water and a mixture of a gas containing an abrasive at a surface for processing which device has a relatively low consumption of abrasive and carrier gas, provides an option erosion effect and effectively avoids the danger of blockage of the abrasive carrying channels and apertures.

These objects are achieved in an improvement in a device for processing a surface of an object such as for cleaning teeth, by directing water and a carrier gas containing an abrasive at the surface, said device including a nozzle having at least one water discharge aperture and a carrier discharge aperture adjacent the water discharge aperture, said water discharge aperture being connected to a channel extending to means for connection to a source of water and said carrier discharge aperture being in communication with a carrier gas channel connectible to a source of gas containing the abrasive. The improvements comprise said carrier gas channel adjacent said carrier gas discharge aperture terminating in a mixing chamber which is in communication with the gas discharge aperture, an additional channel connectible to a source of abrasive-free gas discharging into the mixing chamber for discharge through the gas discharge aperture so that the abrasive-free gas, which is conveyed in said additional channel, can be from a source having a higher acceleration energy in comparison to the carrier gas so the gas containing the abrasive is accelerated as it passes from said mixing chamber through said discharge aperture.

The additional channel preferably terminates in an acceleration jet, which discharges into the mixing chamber and produces a jet of gas in the chamber extending toward the discharge aperture which jet creates a suction to draw in the carrier gas containing the abrasive. The chamber is preferably designed with an outer wall having a funnel-like shape terminating in the discharge opening and having an axis extending on the axis of the acceleration jet. In order to obtain a good mixing of the carrier gas with the abrasive contained therein, preferably the carrier gas channel has an oblique portion terminating in the chamber to create a rotational or swirling motion of the flow of gas in the chamber. Preferably, the water discharge aperture is concentrically arranged around the gas discharge aperture and is displaced along the axis of the gas discharge aperture to provide a setback. In the preferred embodiment wherein the chamber is formed by a funnel-shaped part, the gas discharge aperture is formed by a tubular part which is supported in the water discharge aperture by a plurality of ridges so that the water discharge aperture is formed by a plurality of arcuate segments that surround the gas discharge aperture.

The optimization of the two gas conduits or channels is possible in that the additional channel, which is separate from the carrier gas, is provided with the abrasive-free gas. Given these relatively large cross-sections for the channel and in order to accelerate the relatively slow flow of the abrasive carrier gas, the additional abrasive-free gas is set to a high energy content which is supplied to the carrier gas having an abrasive just before emergence from the gas discharge opening in order to thereby guarantee an optimum erosion of material on the tooth surface. As explained in greater detail hereinbelow, a relative underpressure is generated by means of the structure of the acceleration jet and the mixing chamber in which the carrier gas containing the abrasive will be accelerated by the abrasive-free gas. As a result, a suction effect occurs, which effect will further reduce the danger of blockage in the channel. Another advantage of the nozzle of the present arrangement is that the water surrounds the portion of the nozzle containing the carrier gas with the abrasive in an annular jacket, is added to the carrier gas having the abrasive after the water and gas have been passed through their respective discharge apertures. By so doing, the possibility of giving off dust is restricted. By means of the somewhat setback of the location of the water discharge apertures relative to the location of the carrier gas discharge aperture, the device of the present invention has the additional development that the danger of encrustation due to the contact of the water with the abrasive, when the gas discharge jet engages the surface being treated, can be avoided.

BRIEF DESCRIPTION OF THE DRAWINGS

FIG. 2 is a longitudinal cross-section of a nozzle of the dental handpiece of the present invention;

FIG. 3 is a longitudinal cross-section of a part of the nozzle taken on a plane at 90° in comparison to the plane of the cross-section of FIG. 2;

FIG. 4 is an end view of the nozzle; and

FIG. 5 is a partial end view of the opposite end of the nozzle of FIG. 2.

DESCRIPTION OF THE PREFERRED EMBODIMENTS

Figure 1:
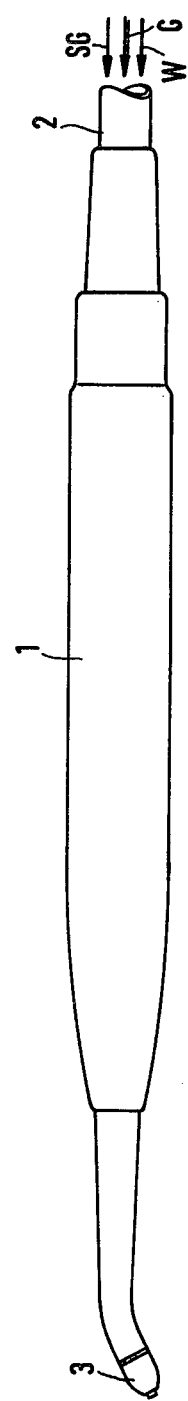
FIG. 1 is a plan view of a dental handpiece in accordance with the present invention.

The principles of the present invention are particularly useful in a dental handpiece having a grasping element 1, which has a nozzle 3 at one end and the opposite end is connected to a supply hose 2. The supply hose 2 has various conduits for separately conveying different agents such as water indicated by the arrow W, a carrier gas which contains an abrasive or an abradant and is indicated by arrow SG, and additional abrasive-free gas indicated by the arrows G.

The nozzle or jet arrangement 3 as best illustrated in FIGS. 2–4 contains a basic body or part 4 designed to be dynamically balanced with two channels 5 and 5a which are provided for receiving an abrasive-free gas indicated by the arrow G in FIG. 1. The body 4 also has a water channel 6 (see FIGS. 3 and 4) as well as an additional channel 7, which contains a carrier gas that contains the abrasive and is indicated by the arrow SG. As illustrated in FIG. 2, the two channels 5 and 5a can either have a common feed conduit or separate individual conduits or channels. The channels 5 and 5a discharge through obliquely extending channel portions 8 and 8a into a channel or bore of an acceleration jet 9 which in turn extends into a chamber 10, which is formed by an end face 11 of the part 4 and by a concentrically disposed funnel-shaped part 12 which converges to a projection that contains a discharge channel 13. The discharge channel 13 forms a gas discharge aperture for both the carrier gas SG, which is mixed with the abrasive, as well as for the abrasive-free gas G.

As illustrated in FIG. 3, the channel 7 terminates in a portion 14, which has a larger cross-section in comparison to the cross-section of the bore of the acceleration jet 9 and directly discharges into the mixing chamber 10 so that the carrier gas with the abrasive can be introduced into the chamber 10. The water channel 6 of the part 4 is connected by an obliquely extending channel portion 15 to a hollow annular space 16 which extends between the funnel-shaped part 12 and an outer sleeve or head member 17 which is concentrically positioned on the base body 4. The front edge of the sleeve 17 is somewhat set back in comparison to the front edge of the discharge channel 13 so that an inadvertent closing of the discharge channel 13, for example, due to contact with the surface being treated, will not cause the emerging water to enter directly into the discharge channel 13 and lead therefore to an encrustation of the abrasive material. Moreover, after the flow of the gas containing the abrasive has been shut off, a suction effect, which is created by the flow of gas through the jet 9 will empty the abrasive conveying conduit or channel of any abrasive residues in the area of the nozzle arrangement. Thus, a blockage of the channel such as 7 and 14 which contains the gas that transports the abrasive material is effectively prevented.

Both the acceleration jet 9 as well as the funnel-shaped part 12 and the sleeve 17 are threaded so that they may be screwed onto the base body 4. Thus, they can be easily removed if desired and are sealed relative to one another by means of corresponding O-rings such as 19 and 20. As a result of the fact that the nozzle can be disassembled, it is possible to easily replace damaged parts when needed.

The following effect is achieved by means of the described nozzle arrangement. A carrier gas mixed with an abrasive, for example, sodium carbonate, is conducted into the chamber 10 from the channel 7 and the portion 14 with a pressure approximately in the range of 1–1.5 bar. The abrasive-free gas, for example, air, is conducted through channels such as 5 and 5a through the acceleration jet 9 with a pressure approximately in a range of between 2 and 2.7 bar. With a jet diameter of approximately 0.6 mm, a flow of approximately 10 liters per minute will occur. As a result of the introduction of this abrasive-free air provided with a relatively high acceleration energy, the gas mixture containing the abrasive that is in the chamber 10 is greatly accelerated and emerges from the discharge channel 13 with a relatively high energy. The acceleration jet 9 thereby produces an open jet of air whose core is propagated in the direction toward the gas discharge aperture 13 and which core, in the manner of a free jet nozzle, produces a relative underpressure or suction in the chamber 10 which contributes to a particularly favorable conveyance of the abrasive. As a result, a certain suction effect for the abrasive arises, which further reduces the danger of blockage and is particularly favorable when the abrasive is conducted into the funnel-shaped chamber 10 through a feed channel 14 which extends obliquely (as illustrated by channel 14a in broken lines) in such a manner that the abrasive gas mixture is placed in a rotating or swirling motion and is thus uniformly mixed with the accelerated core of gas from the acceleration jet 9.

The water is conducted toward the nozzle tip in the annular space 16 and is mixed with the abrasive outside of the discharge channel 13 so that the water forms a sheath around the emerging stream of gas and abrasive to result in an extensive avoidance of the formation of any dust. As can be seen from FIG. 5, the water emerges from four jets 21 which are formed by recesses in the sleeve 17 that provide the support ridges 22 that engage the outside of the projection forming discharge channel 13.

Although various minor modifications may be suggested by those versed in the art, it should be understood that we wish to embody within the scope of the patent granted hereon, all such modifications as reasonably and properly come within the scope of our contribution to the art.

We claim:

1. In a device for processing a surface of an object, such as for cleaning teeth, by directing water and a carrier gas containing an abrasive at said surface, said device including a nozzle having at least one water discharge aperture and a gas discharge aperture adjacent the water discharge aperture, said water discharge aperture being connected to a channel extending to means for connection to a source of water and said carrier gas discharge aperture being in communication with a carrier gas channel connectible to a source of gas containing the abrasive, the improvements comprising said carrier gas channel adjacent said gas discharge aperture terminating in a mixing chamber in communication with said gas discharge aperture, and an additional channel connectible to a source of abrasive-free gas discharging through an acceleration jet into said mixing chamber for discharge through said gas discharge aperture, said acceleration jet creating a flow of the abrasive-free gas in the mixing chamber toward the gas discharge aperture and creating a suction for entraining the carrier gas with the abrasive into the flow of the abrasive-free gas, said chamber having a configuration of a converging annular chamber with an axis disposed on the axis of the acceleration jet so that the abrasive-free gas being conveyed in said additional channel can be from a source having a higher acceleration energy in comparison to the carrier gas sio that the gas containing the abrasive is accelerated as it passes from said mixing chamber through said gas discharge aperture.

2. In a device according to claim 1, wherein the carrier gas channel discharges into the mixing chamber obliquely to an axis of the acceleration jet to create a swirling motion of the carrier gas containing the abrasive to insure uniform mixing of the carrier gas with the abrasive and the abrasive-free gas from the acceleration jet.

3. In a device according to claim 1, wherein the water discharge aperture is concentrically disposed relative to the gas discharge aperture and is displaced along the axis of the gas discharge aperture to create a setback so that closing of the gas discharge aperture does not close the water discharge aperture.

4. In a device for processing a surface of an object, such as for cleaning teeth, by directing water and a carrier gas containing an abrasive at said surface, said device including a nozzle having at least one water discharge aperture and a gas discharge aperture adjacent the water discharge aperture, said water discharge aperture being connected to a channel extending to means for connection to a source of water and said carrier gas discharge aperture being in communication with a carrier gas channel connectible to a source of gas containing the abrasive, the improvements comprising said carrier gas channel adjacent said gas discharge aperture terminating in a mixing chamber in communication with said gas discharge aperture, and an additional channel connectible to a source of abrasive-free gas discharging into said mixing chamber for discharge through said gas discharge aperture, said chamber being formed by a base part and a funnel-shaped part mounted thereon, said funnel-shaped part terminating in a tubular projection forming the gas discharge aperture, said nozzle including a sleeve concentrically arranged around the funnel-shaped part and having an opening receiving the tubular projection and forming a concentrically arranged water discharge opening so that the abrasive-free gas being conveyed in said additional channel can be from a source having a higher acceleration energy in comparison to the carrier gas so that the gas containing the abrasive is accelerated as it passes from said mixing chamber through said gas discharge aperture.

5. In a device according to claim 4, wherein the base part has at least one channel portion for the carrier gas containing the abrasive, at least one channel for the water, at least one channel for the abrasive-free gas, each channel for the abrasive-free gas terminating in an acceleration jet producing a jet of abrasive-free gas concentrically disposed relative to the base part and aligned with the tubular projection of the funnel-shaped part which is mounted concentrically on the axis of said jet.

6. In a device according to claim 5, wherein the acceleration jet, the funnel-shaped part and the sleeve are removably mounted on the base part.

7. In a device for processing a surface of an object, such as for cleaning teeth, by directing water and a carrier gas containing an abrasive at said surface, said device including a nozzle having at least one water discharge aperture and a gas discharge aperture adjacent the water discharge aperture, said water discharge aperture being connected to a channel extending to means for connection to a source of water and said carrier gas discharge aperture being in communication with a carrier gas channel connectible to a source of gas containing the abrasive, the improvements comprising said carrier gas channel adjacent said gas discharge aperture terminating in a mixing chamber in communication with said gas discharge aperture, and an additional channel connectible to a source of abrasive-free gas discharging into said mixing chamber for discharge through said gas discharge aperture, said additional channel terminating in an acceleration jet, which is axially aligned with the gas discharge aperture, said gas discharge aperture having a diameter of 0.8 mm, said acceleration jet having a diameter of 0.6 mm so that the gas flow through the nozzle amounts to approximately 10 liters per minute and so that the abrasive-free gas being conveyed in said additional channel can be from a source having a higher acceleration energy in comparison to the carrier gas so that the gas containing the abrasive is accelerated as it passes from said mixing chamber through said gas discharge aperture.

* * * * *